United States Patent [19]
Hubred

[11] Patent Number: 5,772,890
[45] Date of Patent: *Jun. 30, 1998

[54] CMA PRODUCTION UTILIZING ORGANIC ION EXCHANGE FROM FERMENTATION BROTH

[75] Inventor: Gale L. Hubred, Richmond, Calif.

[73] Assignee: General Atomics International Services Corporation, San Diego, Calif.

[*] Notice: The terminal 28 months of this patent has been disclaimed.

[21] Appl. No.: 931,214

[22] Filed: Aug. 17, 1992

Related U.S. Application Data

[63] Continuation-in-part of Ser. No. 681,143, Apr. 5, 1991, Pat. No. 5,162,214.

[51] Int. Cl.$^6$ .................................................... B01D 11/04
[52] U.S. Cl. .......................................... 210/638; 210/634
[58] Field of Search ....................... 423/54, 63; 435/136, 435/140; 210/634, 638

[56] References Cited

U.S. PATENT DOCUMENTS

| Re. 32,609 | 2/1988 | Gancy . |
|---|---|---|
| 3,944,606 | 3/1976 | Rieger et al. . |
| 3,944,616 | 3/1976 | Rieger et al. . |
| 4,275,234 | 6/1981 | Baniel et al. . |
| 4,377,488 | 3/1983 | Gancy . |
| 4,405,717 | 9/1983 | Urbas . |
| 4,430,242 | 2/1984 | Gancy . |
| 4,444,881 | 4/1984 | Urbas . |
| 4,468,373 | 8/1984 | Nevitt ......................................... 423/54 |
| 4,636,467 | 1/1987 | Chynowith . |
| 4,673,519 | 6/1987 | Gancy . |
| 4,913,831 | 4/1990 | Todd et al. . |
| 5,068,188 | 11/1991 | Wise et al. . |
| 5,162,214 | 11/1992 | Hubred ............................... 435/140 X |

OTHER PUBLICATIONS

Althouse, J.W., et al., Analysis of Organic Extractant Systems for Acetic Acid Removal for Calcium Magnesium Acetate Production, *Ind. Eng. Chem. Res.*, vol. 31, No. 8, 1992.
The Englewood Monthly, North Dakota, Mar. 1991.

*Primary Examiner*—Frank Spear
*Attorney, Agent, or Firm*—Heller, Ehrman, White & McAuliffe

[57] ABSTRACT

A method is provided for removing an anion from an aqueous liquid, such as a fermentation broth. The aqueous broth is contacted with a water-immiscible ion exchange liquid to extract the anion from the broth. The anion exchange liquid is then back extracted with an aqueous phase, to remove the anion, preferably for other uses.

11 Claims, 1 Drawing Sheet

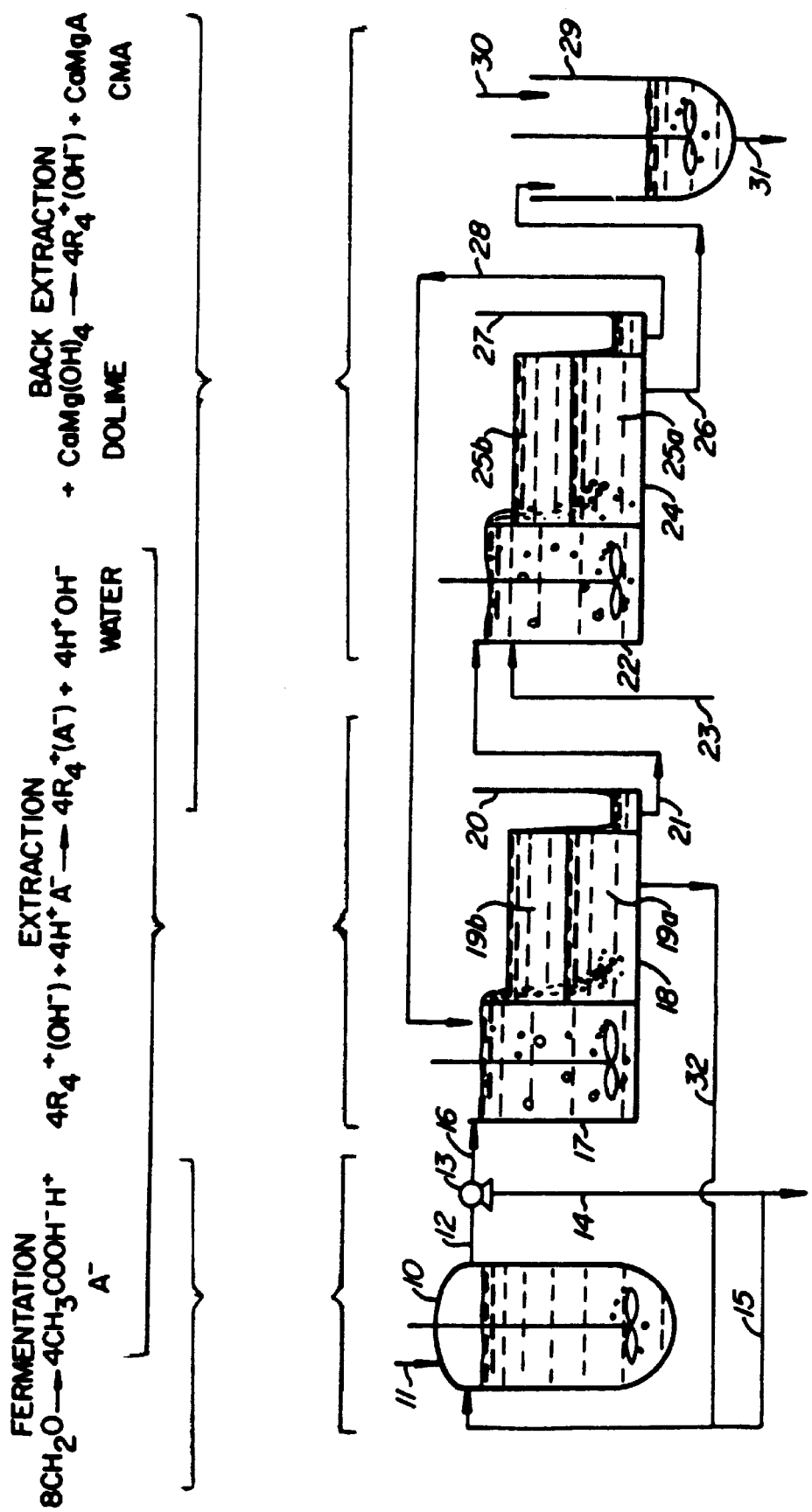

CM A PRODUCTION UTILIZING ORGANIC ION EXCHANGE FROM FERMENTATION BROTH

This is a continuation-in-part of Ser. No. 07/681,143, filed Apr. 5, 1991, now Pat. U.S. No. 5,16214 the disclosure of which is incorporated by reference herein in its entirety. The present invention is directed to a method for removing organic anions from an aqueous liquid, such as a fermentation broth, which can be performed in a continuous manner.

The method is particularly useful for exchanging organic anions, particularly organic acid anions, from an organic anion-producing fermentation broth for a back-extraction ion and directing the extracted anion to a reaction vessel where it may be used in an anion-consuming chemical process while disposing of the back extraction ion by a neutralizing reaction. The method is particularly useful for extracting acetate ion from an acetate-producing fermentation broth and using the extracted acetate to make calcium-magnesium acetate (CMA).

BACKGROUND OF THE INVENTION

According to the present invention an anion is recovered from an aqueous liquid, such as organic acid anion from an organic acid anion-producing fermentation broth, by extraction with a non-aqueous ion exchange liquid. The present invention is particularly advantageous for extracting anions from fermentation broths since fermentation which produces, for example, acetic acid, is limited because the accumulated level of acetic acid inhibits further biological production.

Many fermentation processes also result in decrease in production of the desired anion when pH change due to fermentation is sufficient to inhibit the organisms.

The anion-containing liquid need not be a fermentation broth. Liquids which may be utilized include chemical process effluent streams, waste water, industrial streams, etc.

One method which may be utilized to remove the anion (such as acetate) is to extract it using an extraction solvent which takes advantage of solubility partition coefficients. This, however, has inherent inefficiencies since the anion must be first converted to a species soluble in the non-aqueous extraction liquid, which is usually accomplished by altering the pH of the liquid containing the anion.

Other methods involve removal of the anion, such as citric acid, by a membrane separator, which may be slow and involve specialized membrane technology.

If the anion, such as acetate, is to be used as a feed for a chemical process, another way of removing it is to add the other reactants of the chemical process directly to the fermentation broth. For example, dolomitic lime might be added directly to a fermentation broth containing acetic acid to make CMA. This, however, contaminates the fermentation broth. Therefore, by direct addition of lime to the broth, either the culture cannot be used in a continuous manner, or the fermentation broth must be continuously replenished.

However, it is not believed that a method has been heretofore known for removing anions from an aqueous liquid, such as a fermentation broth, in a continuous manner by using an ion exchange liquid for extraction, whereby the anion is extracted from the liquid in a continuous manner, then back-extracted from the ion-exchange liquid and used directly as a starting material for a chemical process. The present invention provides such a method and, additionally, has the advantageous feature of neutralizing the acid produced in the broth with hydroxyl ion to produce water. Furthermore, by back-extraction, direct contact of the chemical reactants (lime) with the broth is avoided, thereby minimizing undesirable perturbations of the extraction process from the broth.

SUMMARY OF THE INVENTION

The present invention provides a method for removing an anion from an aqueous liquid comprising the steps of contacting the aqueous anion-containing liquid with a non-aqueous extraction liquid comprising an anion exchange reagent which exchanges a back extraction anion with the anion in the aqueous liquid to thereby extract the anion from the aqueous liquid; separating the extraction liquid containing the extracted anion from the aqueous liquid; contacting the extraction liquid containing the extracted anion with a second aqueous phase preferably comprising reactants which react with the anion to form a water-soluble product dissolved in the second aqueous phase; separating the second aqueous phase containing the dissolved product from the extraction liquid;

optionally isolating the product from the second aqueous phase. The method is particularly useful when the anion-containing liquid is a fermentation broth which produces acetate anion and the second aqueous phase comprises calcium and magnesium hydroxide which exchange with the acetate for hydroxide to form water-soluble calcium-magnesium acetate, which also neutralizes acid to form water.

DESCRIPTION OF THE DRAWINGS

FIG. 1 is a schematic view of a preferred apparatus used to perform the present invention.

DESCRIPTION OF THE PREFERRED EMBODIMENTS

The present invention is useful for removing an anion, such as a fermentation product, from an aqueous liquid by extraction using an ion exchange reagent. The extraction liquid containing the ion exchange reagent is then back extracted with a second aqueous phase which may contain reactants which react 20 with the anion and which donate a back-extraction ion to the extraction liquid. Therefore, by recycling the extraction liquid, there is a net flow of back-extraction ion into the aqueous liquid, which back-extraction anion is preferably a base, thereby providing a means for controlling the pH of the aqueous liquid.

Preferred anions are the organic acid anions, such as, formate, acetate, propionate, and the like. Other anions include, citrate, pyruvate, malate and tartrate.

The preferred ion exchange liquids are quaternary ammonium compounds, such as those known in the ALIQUAT® series made by Henkel and ETHOQUAD® made by Akzo. The back-extracting anion is preferably hydroxide ion, provided preferably from calcium and magnesium hydroxides.

The invention will be described in connection with FIG. 1 which shows the preferred embodiment of the present invention. Referring to FIG. 1, the fermentor 10 containing a fermentation broth is maintained under fermentation conditions to produce the product, preferably acetate. Acetate-producing microorganisms and conditions for their fermentation are known in the art. The culture nutrients may be fed into the fermentor 10 through line 11. Broth is then removed through line 11 and the cells are separated by separator 13, such as a centrifuge, and directed through line 14 from which they can be disposed or recycled through line 15 into fermentor 10. The clarified broth is conducted via line 16 into extractor 17 containing the non-aqueous extraction ion exchange liquid. The clarified aqueous broth and the non-aqueous extraction liquid are mixed in the extractor 17 by stirring and as extractor 17 is filled the overflow spills into separation tank 18 where the contents are allowed to separate into two phases 19A and 19B. As shown, 19B is the non-aqueous phase comprising the ion exchange liquid and the anion which has now been extracted from the aqueous phase 19A. The non-aqueous phase spills into collector 20 from which it is drained via line 21 and directed into the back extractor 22. The aqueous slurry containing calcium and magnesium hydroxide (preferably in the form of dolime) is introduced into the back extractor 22 via line 23. The contents of the back extractor 22 are stirred whereby the calcium and magnesium ions react with the acetate ion to form water-soluble calcium-magnesium acetate. The overflow from tank 22 is spilled into settling tank 24 in which the liquids are allowed to settle into two phases 25A and 25B. As shown, the lower aqueous phase 25A contains the dissolved desired product calcium-magnesium acetate which can be withdrawn via line 26. The organic phase containing the ion exchange liquid 25B, now having a hydroxide counter-ion, is spilled into collecting tank 27 and recycled via line 28 into the extractor 17. The calcium-magnesium acetate-containing slurry may be then directed into a processing tank 29 in which the pH may be adjusted by adding acetic acid via line 30. The calcium-magnesium acetate slurry at the desired pH is then withdrawn through line 31. The broth from tank 18 may be recycled into the fermentor 10 via line 32.

To make CMA, preferably the clarified fermentation broth entering tank 17 through line 16 will be at a pH around 6. The aqueous broth recycle phase 19A will be at a pH of about 6.5 and the CMA slurry 25A in tank 24 will be at a pH of about 8. In the processing tank 29 the CMA may be adjusted preferably to a pH of about 7.

Other modifications will be readily perceived from the above description to include, but not limited to, the following. The anion exchange liquid may be diluted with a solvent, such as kerosene, to control the volume and concentration of the ion exchange reagent. To keep the back extraction ion concentration sufficiently high to drive the entire process, the back extraction liquid (introduced through line 23) should be maintained at a relatively high pH, preferably above pH 11.

The CMA slurry exiting line 31 may be recovered as desired, such as by drying, evaporation, crystallization or a combination thereof. The preferred method is to react residual lime (dolime) with additional acetic acid and crystallize the product.

Among the useful anion exchange liquids are in the quaternary amine compounds under the trademark ALIQUAT® made by Henkel. The broth which is introduced into She extraction tank 17 should be cell-free and may be made so by centrifugation, filtration or other convenient means.

To test the amount of acetate ion exchange as a function of pH, a feed comprising 50 gm/liter vinegar was utilized and extracted with an organic phase comprising 10 vol% ALIQUAT® 336 in kerosene. The results are shown in the following table.

| Feed pH | Ave. Dist. Ratio D | Minimum Acetate g/l |
|---------|-------------------|---------------------|
| 2.5 | 0.3 | 8 |
| 4.5 | 0.7 | 3 |
| 6.0 | 1.2 | 0.3 |

Feed: 50 g/l vinegar (acetic acid)
Organic: 10 vol % ALIQUAT® 336 in kerosene

As can be seen from the table, as the pH of the feed material is increased, the distribution ratio between the organic phase and the aqueous phase increases and the amount of acetate remaining in the aqueous phase decreases.

What is claimed is:

1. A method for extracting an anion from an aqueous medium comprising the steps of (a) contacting an aqueous anion containing liquid with a water-immiscible extraction liquid comprising a quaternary ammonium compound which exchanges a hydroxide ion with said anion to thereby extract said anion from said aqueous liquid into said extraction liquid;

(b) separating said extraction liquid containing said anion from said aqueous liquid;

(c) contacting said extraction liquid containing said anion with a second aqueous phase comprising reactants which react with said anion to form a water-soluble product dissolved in said second aqueous phase;

(d) separating said second aqueous phase containing said dissolved product from said extraction liquid.

2. The method according to claim 1 wherein said anion comprises organic acid anions.

3. The method according to claim 1 wherein said reactants in step (c) comprise calcium and magnesium hydroxide or oxide.

4. A method according to claim 2 wherein said aqueous anion-containing liquid comprises a fermentation broth.

5. A method according to claim 4 wherein said broth is substantially cell-free.

6. A method according to claim 1 wherein said water-immiscible extraction liquid further comprises an organic diluent.

7. A method according to claim 6 wherein said diluent comprises kerosene.

8. A method according to claim 1 wherein said second aqueous phase comprises dolomitic lime.

9. A method according to claim 1 wherein said method is performed in a continuous manner and at least a portion of said extraction liquid in said step (d) is recycled for use in said step (c).

10. A method according to claim 9 wherein at least a portion of said aqueous liquid from said step (b) is recycled for use in fermentation to form said aqueous anion containing liquid.

11. A method according to claim 3 wherein said step (d) comprises evaporation of liquids to produce solid calcium-magnesium salt of said anion.

* * * * *